US008257249B2

United States Patent
Sugisawa

(10) Patent No.: US 8,257,249 B2
(45) Date of Patent: Sep. 4, 2012

(54) FLEXIBLE TUBE FOR ENDOSCOPE AND METHOD OF MANUFACTURING THE SAME

(75) Inventor: Tatsuya Sugisawa, Saitama (JP)

(73) Assignee: FUJIFILM Corporation, Tokyo (JP)

( * ) Notice: Subject to any disclaimer, the term of this patent is extended or adjusted under 35 U.S.C. 154(b) by 627 days.

(21) Appl. No.: 12/400,973

(22) Filed: Mar. 10, 2009

(65) Prior Publication Data

US 2009/0234190 A1    Sep. 17, 2009

(30) Foreign Application Priority Data

Mar. 12, 2008 (JP) ................................. 2008-062435
Mar. 12, 2008 (JP) ................................. 2008-062731

(51) Int. Cl.
*A61B 1/00* (2006.01)
(52) U.S. Cl. .................. 600/140; 600/128; 600/139
(58) Field of Classification Search .............. 600/128, 600/139, 140
See application file for complete search history.

(56) References Cited

U.S. PATENT DOCUMENTS

| 5,394,864 A | 3/1995 | Kobayashi et al. | |
| 5,885,207 A * | 3/1999 | Iwasaka | 600/139 |
| 2002/0028984 A1 * | 3/2002 | Hayakawa et al. | 600/139 |
| 2003/0220543 A1 * | 11/2003 | Abe | 600/140 |
| 2007/0255105 A1 * | 11/2007 | Ochi et al. | 600/139 |

FOREIGN PATENT DOCUMENTS

| DE | 42 34 833 A1 | 4/1993 |
| JP | 59-137030 A | 8/1984 |
| JP | 61-046923 A | 3/1986 |
| JP | 61-256085 A | 11/1986 |
| JP | 2001-070235 A | 3/2001 |

OTHER PUBLICATIONS

EP Communication, dated Jul. 20, 2009, issued in corresponding EP Application No. 09003479.4, 7 pages.

* cited by examiner

*Primary Examiner* — Matthew J Kasztejna
*Assistant Examiner* — Kevin G Barry, III
(74) *Attorney, Agent, or Firm* — Sughrue Mion, PLLC

(57) ABSTRACT

A flexible tube for an endoscope comprises: a spiral tube including a band-shaped plate which is spirally wound; a braid which covers an outer circumferential surface of the spiral tube; and an outer skin made of a resin, which covers an outer circumferential surface of the braid, wherein the braid includes metal fibers deposited with a release agent and heat-resistant resin fibers deposited with a bonding material, the metal fibers and the resin fibers are blended in a mesh pattern, and the braid is bonded to the outer skin by the bonding material.

5 Claims, 5 Drawing Sheets

FLEXIBLE TUBE FOR ENDOSCOPE AND METHOD OF MANUFACTURING THE SAME

BACKGROUND OF THE INVENTION

The present invention relates to a flexible tube for an endoscope which is used for medical care, and a method of manufacturing the flexible tube for an endoscope.

Up to now, a flexible tube for an endoscope, which is inserted into a living body such as a human body and used for diagnosis and treatment of organs, extraction of samples, and the like, includes a spiral tube (flex) in which a thin band-shaped plate is wound spirally, a braid (net) covering an outer circumferential surface of the spiral tube, and a resin outer skin covering an outer circumferential surface of the braid.

In the conventional flexible tube for an endoscope having the structure as described above, the braid is provided between the spiral tube and the outer skin and bonded to an inner circumferential surface of the outer skin to serve as a rigidity reinforcing material of the flexible tube. In other words, unlike a case where the spiral tube is covered with only the outer skin, the braid reinforces the rigidity of the flexible tube.

The braid as described above is normally formed by knitting metal fibers such as stainless steel fibers or brass fibers. Therefore, for example, when a general resin outer skin is formed on the outer circumferential surface of the braid by a general formation method such as extrusion molding, there are many cases where the bonding (contact or joining) strength between the braid and the outer skin of the flexible tube is reduced during the use of the endoscope because chemical bonding between metal and a resin is basically only weak bonding with intermolecular forces.

The chemical bonding between metal and a resin is vulnerable to water. Therefore, when the endoscope is used under the presence of moisture such as water or steam or when the endoscope is frequently cleaned with water, a disinfection solution, a cleaning solution, or the like, the bonding strength between the braid and the outer skin of the flexible tube is quickly reduced.

When the bonding strength between the braid and the outer skin is reduced in the flexible tube for an endoscope as described above, the function of the braid serving as the rigidity reinforcing material of the flexible tube deteriorates to reduce the rigidity of the flexible tube, with the result that the use of the endoscope is adversely affected in many cases. In addition, when the bonding strength between the braid and the outer skin is reduced in the flexible tube, the braid and the outer skin may be peeled off from each other to buckle the flexible tube, thereby disabling the use of the endoscope.

To address this problem, JP 59-137030 A discloses a flexible tube for an endoscope, in which a net-tube-shaped braid formed by knitting a fiber material is bonded (joined) to an outer skin (outer tube) by a cohesive agent.

JP 61-256085 A discloses a flexible tube for an endoscope, in which fibers made of a thermoplastic resin are intervolved with at least one metal wire of a metal wire group composing a braid and melted to bond the braid to an outer skin.

JP 61-046923 A discloses a flexible tube for an endoscope, in which a release agent is interposed between the spiral tube (flex) and the braid, and the braid and an outer skin made of a synthetic resin are bonded (jointed) to each other by a polyester-based urethane bonding material which is applied on the surface of the braid and contains toluene diisocyanate as a monomer.

In the flexible tube for an endoscope disclosed in JP 59-137030 A, the braid and the outer skin are bonded to each other by the cohesive agent. Therefore, while the flexible tube is prevented from hardening that occurs when the bonding material is used, the braid and the outer skin of the flexible tube can be prevented from being peeled off from each other, that is, the bonding strength can be prevented from reducing. However, the cohesive agent is generally made of a resin and thus the bonding thereof to metal is weak, and hence the reduction in bonding strength between the braid and the outer skin is not substantially different from that in conventional flexible tubes for an endoscope.

In the flexible tube for an endoscope disclosed in JP 61-256085 A, a part of the braid is the fibers made of a thermoplastic resin, and hence the braid is connected to the fibers serving as bonding materials by physical force. When the fibers are melted, the braid and the outer skin are bonded to each other, and hence the bonding strength (contact strength or joining strength) between the braid and the outer skin may be higher than that in the flexible tube in which the braid and the outer skin are bonded to each other by only the bonding material. However, as the flexible tube, that is, the endoscope is used over time, the bonding strength between the braid and the outer skin is reduced to lower the rigidity of the flexible tube.

In the flexible tube for an endoscope disclosed in JP 61-046923 A, the braid and the outer skin are bonded to each other by the polyester-based urethane bonding material containing the toluene diisocyanate as the monomer. Therefore, the bonding between the braid and the outer skin is stronger than that in a conventional flexible tube using a bonding material. However, the braid and the outer skin are bonded to each other fundamentally by the bonding material made of a resin. Thus, even though an endurance time is longer than that in the conventional flexible tube using the bonding material, the bonding strength between the braid and the outer skin is eventually reduced.

SUMMARY OF THE INVENTION

An object of the present invention is to provide a flexible tube for an endoscope with high endurance, in which a bonding strength between a braid and an outer skin in the flexible tube is not reduced by a temporal change related to a use period of the endoscope or by moisture in a use environment (including cleaning environment) of the endoscope even when an endoscope is continuously used. Another object of the present invention is to provide a method of manufacturing such a flexible tube for an endoscope.

A flexible tube for an endoscope according to the present invention comprises: a spiral tube including a band-shaped plate which is spirally wound; a braid which covers an outer circumferential surface of the spiral tube; and an outer skin made of a resin, which covers an outer circumferential surface of the braid, wherein the braid includes metal fibers deposited with a release agent and heat-resistant resin fibers deposited with a bonding material, the metal fibers and the resin fibers are blended in a mesh pattern, and the braid is bonded to the outer skin by the bonding material.

According to the present invention, there is provided a method of manufacturing a flexible tube for an endoscope, the flexible tube including: a spiral tube including a band-shaped plate which is spirally wound; a braid which covers an outer circumferential surface of the spiral tube and includes a metal fiber and a resin fiber having a heat resistance; and an outer skin made of a resin, which covers an outer circumferential surface of the braid, the method comprising the steps of: depositing a release agent on the metal fibers; depositing a bonding material on the resin fibers; forming the braid by blending the metal fibers and the resin fibers in a mesh pattern; covering the outer circumferential surface of the spiral tube with the braid; covering the outer circumferential surface of the braid with the outer skin; and bonding the braid and the outer skin to each other by the bonding material deposited on the resin fibers.

DETAILED DESCRIPTION OF THE PREFERRED EMBODIMENT

Hereinafter, an embodiment of the present invention is described in detail.

Figure 1:
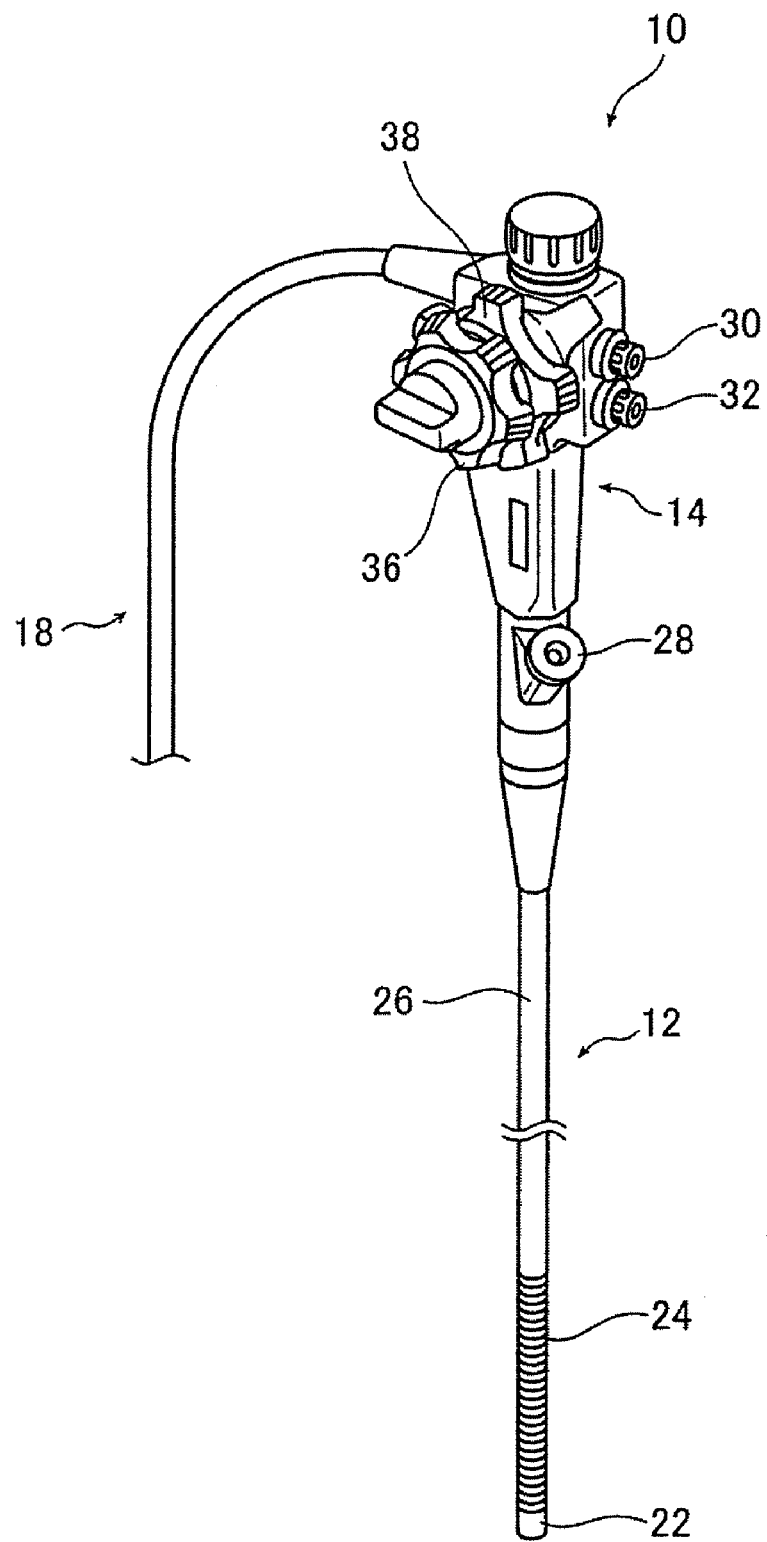
FIG. 1 is a perspective view illustrating an entire structure of an endoscope using a flexible tube according to an embodiment of the present invention.

FIG. 1 illustrates an endoscope 10 using a flexible tube according to the embodiment of the present invention.

The endoscope 10 is inserted into an inspection region such as a body cavity (alimentary canal or ear-nose-throat region) to observe the inspection region, to take pictures or moving images, and to extract samples, and includes an insertion portion 12, an operating portion 14, and a universal code (LG soft portion) 18.

The insertion portion 12 is a long part inserted into the inspection region such as the body cavity, and includes a tip end portion 22, an angle portion (bending portion) 24, and a flexible tube 26 according to the embodiment of the present invention. The tip end portion 22 is connected to a tip end of the flexible tube 26 through the angle portion 24.

The operating portion 14 is a part for operating the endoscope 10 and includes, as in the case of a general endoscope, a forceps port 28 for inserting forceps, a suction button 30 for performing suction from an air/water supply nozzle of the tip end portion 22, and an air/water supply button 32 for supplying air or water. The operating portion 14 further includes operating knobs 36 and 38 as operating means for bending the angle portion 24 of the insertion portion 12 to adjust the orientation of the tip end portion 22.

The universal code 18 is a part for connecting the operating portion 14 to a connector (not shown) for connecting water supply means, air supply means, and suction means to the endoscope 10.

The endoscope 10 illustrated in FIG. 1 has parts inserted therein, such as a lightguide for illuminating the inspection region, an air/water supply channel connected to the air/water supply nozzle, a forceps channel for inserting forceps, and a cable for photographing the inspection region (image guide for observation), which are not illustrated.

The flexible tube 26 is a part for connecting the tip end portion 22 and the angle portion 24 to the operating portion 14, which is a long part having sufficient flexibility to be inserted into the inspection region. The lightguide, the air/water supply channel, the forceps channel, and the cable as described above are enclosed in the flexible tube 26.

Figure 2:
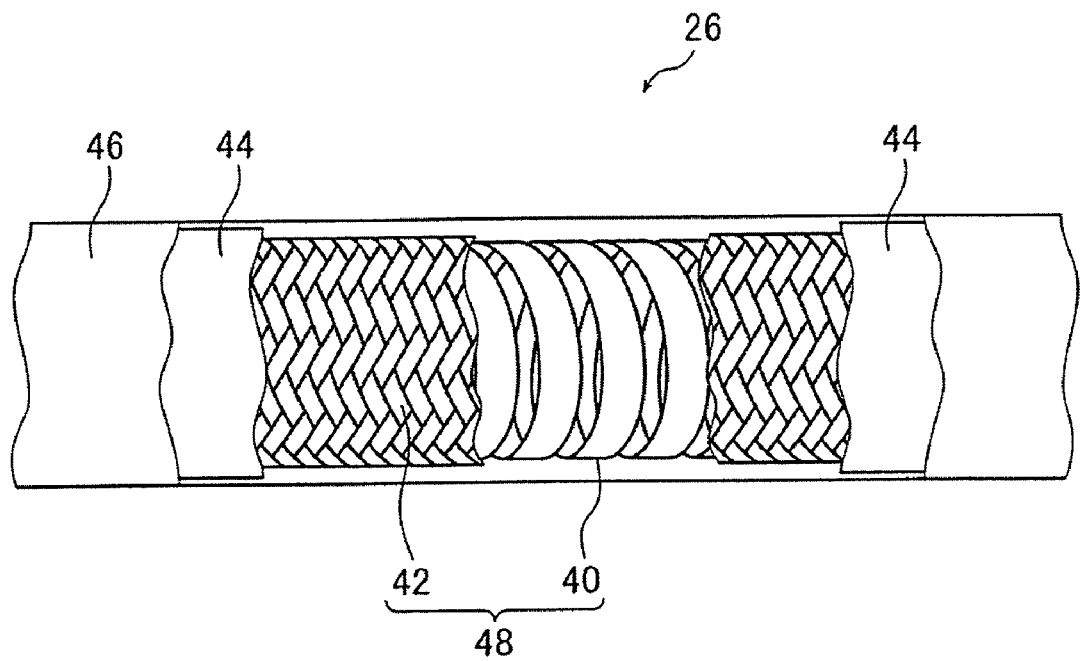
FIG. 2 is a partially cutaway view illustrating a concept of the flexible tube for an endoscope according to the embodiment of the present invention.

As illustrated in FIG. 2, the flexible tube 26 includes a spiral tube (flex) 40 formed by spirally winding a thin band-shaped plate, a braid (net) 42 covering an outer circumferential surface of the spiral tube 40, and a resin outer skin 44 covering an outer circumferential surface of the braid 42. The braid 42 is formed by blending metal fibers deposited with release agent and heat-resistant resin fibers deposited with bonding material in a mesh pattern. An outer circumferential surface of the resin outer skin 44 is preferably covered with a coat layer 46.

Here, a hollow tubular body in which the outer circumferential surface of the spiral tube 40 is covered with the braid 42 is referred to as an inner tube (intermediate product) 48.

The braid 42 serves as a reinforcing member for covering the outer circumferential surface of the spiral tube 40 to reinforce the rigidity of the flexible tube 26, and has a structure in which the metal fibers deposited with the release agent and the heat-resistant resin fibers deposited with the bonding material are blended in the mesh pattern.

As described in the "BACKGROUND OF THE INVENTION" section, the bonding between metal and a resin is basically very weak bonding with only intermolecular forces and particularly weak to moisture such as water or steam, and hence the bonding (contact or joining) strength between the braid made of metal and the outer skin made of a resin is reduced by the temporal change related to the use time of the endoscope or by the moisture in the use environment and cleaning environment. In addition, even when a bonding material is used to increase the bonding strength between the braid made of metal and the outer skin made of a resin, the bonding strength between the braid made of metal and the bonding material is weak because the bonding material is also generally made of a resin, and hence the bonding material cannot sufficiently bond the braid and the outer skin to each other. Therefore, the bonding strength between the braid made of metal and the outer skin made of a resin is reduced during the use of the endoscope.

In contrast to this, for example, according to the flexible tube disclosed in JP 61-256085 A, the fibers which constitute a part of the braid and made of a thermoplastic resin are melted to strongly bond the braid and the outer skin to each other.

Figure 3:
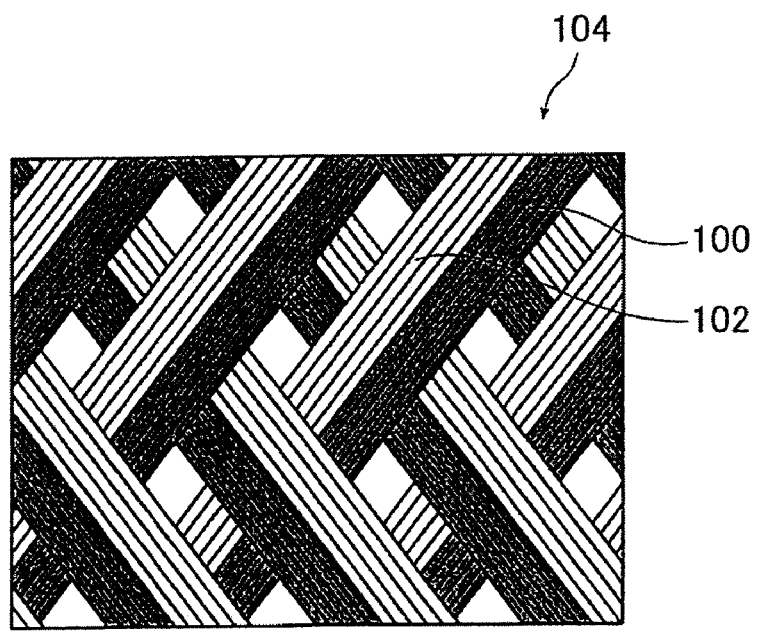
FIG. 3 is a partially enlarged view illustrating a braid used for a flexible tube according to a comparative example.
Figure 4:
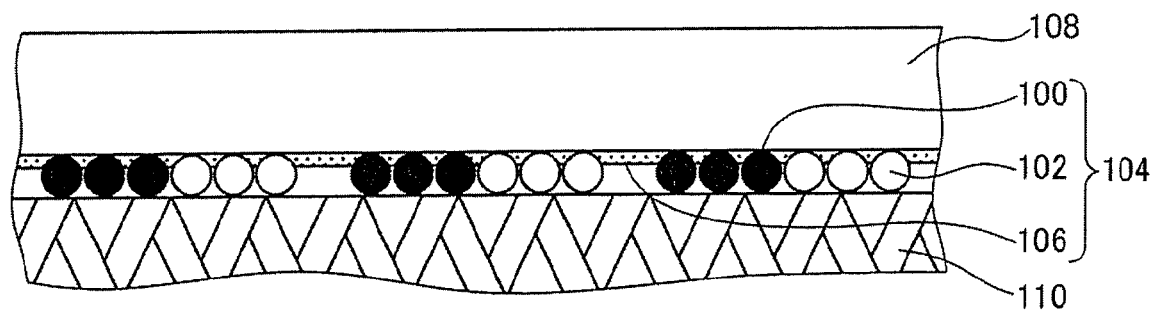
FIG. 4 is a partially enlarged cross sectional view illustrating the flexible tube shown in FIG. 3.

The inventor of the present invention has designed a flexible tube in which a braid 104 includes metal fibers 100 and resin fibers 102 which are blended as illustrated in FIG. 3 and a bonding material 106 is applied to the entire braid 104 to bond the braid 104 and an outer skin 108 to each other by the bonding material 106 as illustrated in FIG. 4. Even in such a flexible tube, the resin fibers 102 are strongly bonded to the outer skin 108 made of a resin by the bonding material 106.

However, the flexible tube disclosed in JP 61-256085 A and the flexible tube illustrated in FIG. 3 cannot solve the problem that the bonding strength between the braid and the outer skin is reduced by the temporal change related to the use time of the endoscope or by the moisture in the use environment and cleaning environment, thereby lowering the rigidity of the flexible tube.

The reason for the above-mentioned problem may be as follows: the melted thermoplastic resin in JP 61-256085 A or the bonding material 106 applied to the entire braid 104 in the flexible tube illustrated in FIG. 3 causes a bonding force between the metal portion (metal fibers) of the braid and the outer skin, and the strength of the bonding force therebetween is included in the strength of the bonding between the braid and the outer skin immediately after the flexible tube is manufactured. In other words, because of the temporal change related to the use time or the moisture in the use environment and cleaning environment, the bonding strength between the metal portion of the braid and the outer skin is reduced relatively faster than the bonding strength between the resin portion of the braid and the outer skin, with the result that the bonding strength between the entire braid and the outer skin is reduced.

Therefore, according to the present invention, the outer skin made of a resin is bonded to only the resin portion of the braid to prevent the outer skin from being bonded to the metal potion of the braid, whereby the flexible tube is realized in which the reduction in bonding strength between the braid and the outer skin can be suppressed.

Figure 5:
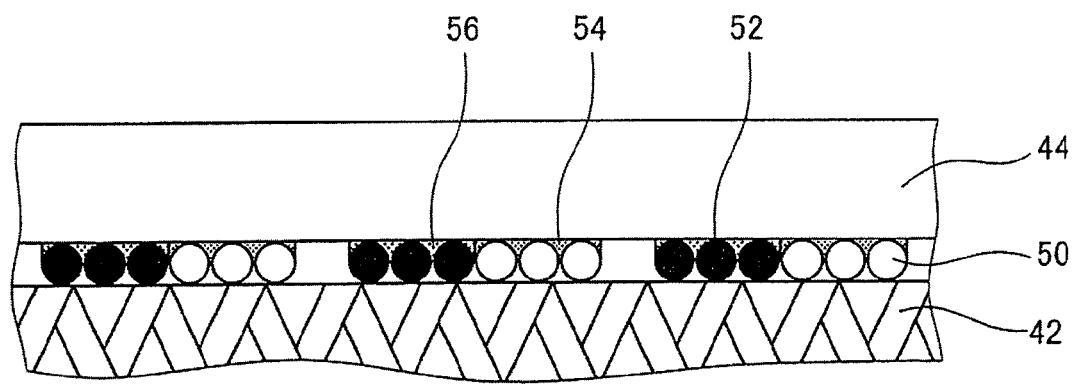
FIG. 5 is a partially enlarged cross sectional view illustrating the flexible tube for an endoscope according to the embodiment of the present invention.

As illustrated in FIG. 5, in this embodiment, the braid 42 is used in which heat-resistant resin fibers 50 deposited with bonding materials 54 and metal fibers 52 deposited with release agents 56 are blended in a mesh pattern. Because of the presence of the bonding materials 54, the resin fibers 50 are bonded to the outer skin 44 made of a resin at sufficient bonding strength. In contrast to this, because of the presence of the release agents 56, the metal fibers 52 are not bonded to the outer skin 44. The braid 42 covers the outer circumferential surface of the spiral tube 40 and is located between the spiral tube 40 and the outer skin 44 to serve as a rigidity reinforcing material of the flexible tube 26.

When the braid 42 as described above is used, the flexible tube 26 hardly exhibits the reduction in bonding strength between the braid 42 and the outer skin 44 due to the temporal change related to the use time of the endoscope or the presence of moisture in the use environment and cleaning environment, that is, the reduction in rigidity of the flexible tube 26. Therefore, the endoscope 10 with high endurance can be realized.

Figure 6:
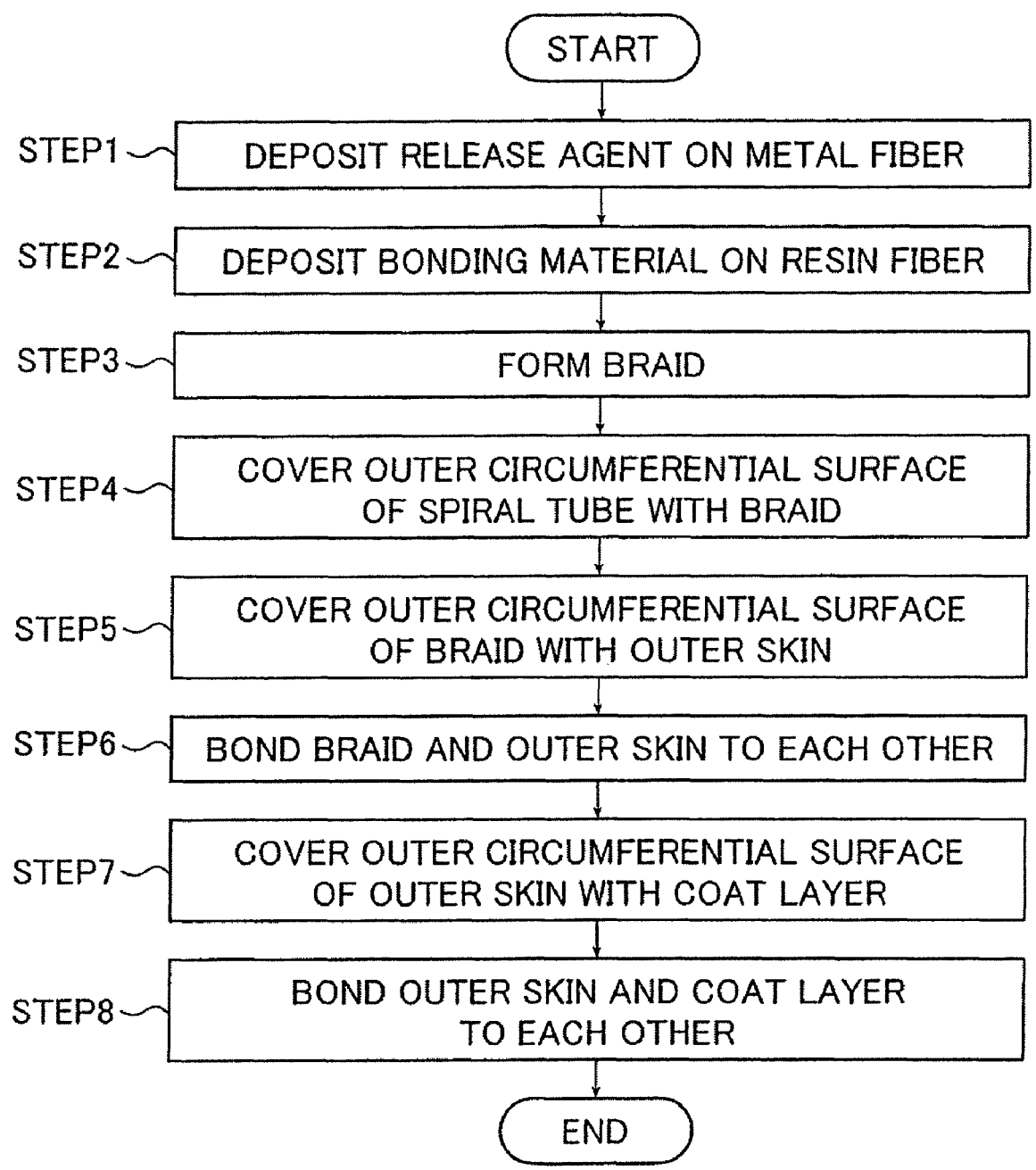
FIG. 6 is a flow chart illustrating a method of manufacturing the flexible tube for an endoscope.

A method of manufacturing the flexible tube 26 for an endoscope as described above is described with reference to a flow chart of FIG. 6.

In STEP 1, the release agents 56 are deposited on the metal fibers 52.

General metal fibers for a braid of a conventional flexible tube may be used for the metal fibers 52 as long as the metal fibers can exert a sufficient rigidity effect on the flexible tube 26 and be deposited with the release agents 56. For example, fibers which are made of stainless steel and have a diameter of 0.1 mm can be used as the metal fibers 52.

A material of the release agents 56 deposited on the metal fibers 52 is not particularly limited as long as the material can serve as the release agent even under exposure to a high-temperature state during the manufacturing of the flexible tube 26. For example, a silicon-based resin or a fluorine-based resin can be used.

The release agents 56 may be disposed in any quantity as long as a surface state of the metal fibers 52 of the braid 42 is maintained so as not to weld the metal fibers 52 of the braid 42 to the outer skin 44. For example, it is desirable to deposit the release agents 56 on the surface of the metal fibers 52 to obtain a thickness of 1 μm to 100 μm.

An example of the method of depositing the release agents 56 on the metal fibers 52, which can be employed, includes a method of immersing the metal fibers 52 in a bath filled with the release agents 56 for a predetermined period of time and then lifting up, from the bath, the metal fibers 52 to be dried. In addition to this, the release agents 56 can be deposited on the metal fibers 52 by a known application method.

Next, in STEP 2, the bonding materials 54 are deposited on the resin fibers 50.

A material of the resin fibers 50 is not particularly limited as long as the material has a sufficient resistance to heat applied during the manufacturing of the flexible tube 26. General heat-resistant resin fibers for a braid of a conventional flexible tube can be used.

The bonding materials 54 deposited on the resin fibers 50 are required to bond the braid 42 and the outer skin 44 to each other so as not to reduce the bonding strength between the resin fibers 50 of the braid 42 and the outer skin 44 during the use of the endoscope 10. The bonding materials 54 which can be used are preferably a polyester-based resin or a polystylene-based resin, more preferably a polyurethane-based resin which is a thermoplastic polyurethane-based elastomer and has a high bonding strength with the outer skin 44.

The quantity of the bonding materials 54 deposited on the resin fibers 50 is required to obtain a sufficient bonding strength between the resin fibers 50 of the braid 42 and the outer skin 44. For example, it is preferable to use the bonding materials 54 having a weight equal to or larger than approximately 10% of a weight of the resin fibers 50.

An example of the method of depositing the bonding materials 54 on the resin fibers 50, which can be employed, includes a method of immersing the resin fibers 50 in a bath filled with the bonding materials 54 for a predetermined period of time and then lifting up, from the bath, the resin fibers 50 to be dried. In addition to this, the bonding materials 54 can be deposited on the resin fibers 50 by a known application method.

In STEP 3, the metal fibers 52 deposited with the release agents 56 and the resin fibers 50 deposited with the bonding materials 54 are blended in the mesh pattern to form the braid 42.

Figure 7:
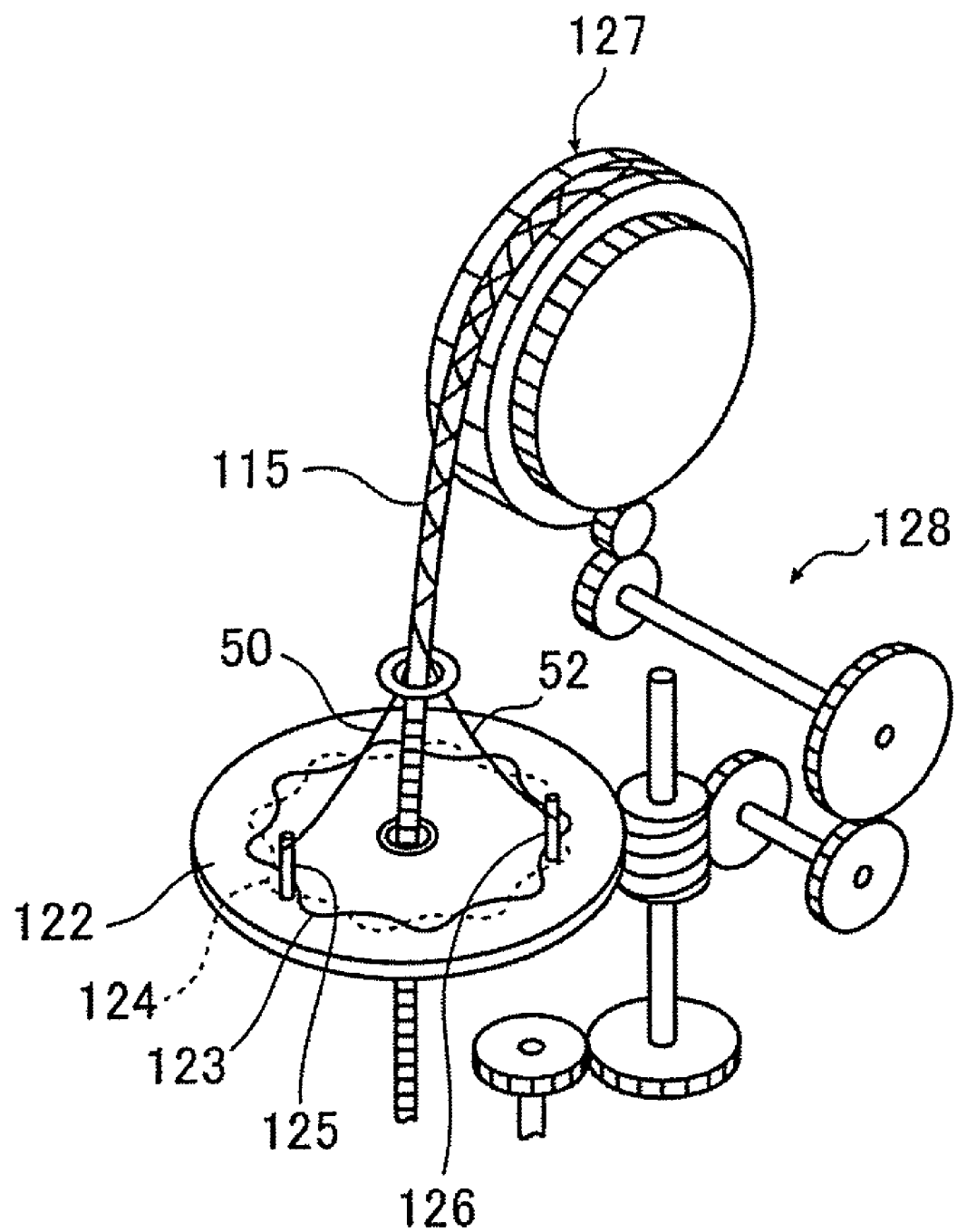
FIG. 7 is a concept view illustrating a weaving machine used in the method of manufacturing the flexible tube for an endoscope.

For example, the braid 42 can be formed by a weaving machine as illustrated in FIG. 7. The weaving machine is disclosed in JP 2001-070235 A and includes a guide circular plate 122. Two thread guide grooves 123 and 124 are formed in the surface of the guide circular plate 122 and circularly snake so as to intersect with each other at a plurality of intersections. A plurality of bobbins 125 is guided by the guide groove 123, that is, one of the two grooves, so as to be moveable in the same direction. The plurality of resin fibers 50 are bound and wound around each of one half of the bobbins 125, and the plurality of metal fibers 52 are bound and wound around each of the other half of the bobbins 125. Similarly, a plurality of bobbins 126 is guided by the guide groove 124, that is, the other of the two grooves, so as to be moveable in the same direction. The plurality of resin fibers 50 are bound and wound around each of one half of the bobbins 126, and the plurality of metal fibers 52 are bound and wound around each of the other half of the bobbins 126.

The weaving machine further includes a pulley 127 rotatably driven by a gear mechanism 128. A long cylindrical member 115 made of a resin is wound around the pulley 127.

The plurality of bobbins 125 and 126 are moved along the guide grooves 123 and 124 by a moving mechanism (not shown) to each feed the resin fibers 50 and the metal fibers 52, and the pulley 127 is rotated to move the cylindrical member 115, whereby the braid 42 can be formed by knitting on an outer circumferential surface of the cylindrical member 115.

The braid 42 formed by knitting is cut at a predetermined length and the cylindrical member 115 made of a resin is removed to form the braid 42 having a cylindrical shape.

In FIG. 5, a composition ratio between the metal fibers 52 and the resin fibers 50 in the braid 42 is approximately 1:1. As long as the rigidity of the flexible tube 26 and the bonding strength between the braid 42 and the outer skin 44 resulting from the bonding between the resin fibers 50 and the outer skin 44 can be sufficiently ensured, the composition ratio between the metal fibers 52 and the resin fibers 50 is not particularly limited. For example, the braid 42 can be constructed such that an area ratio among the metal fibers 52, the resin fibers 50, and a space is 5:4:1.

A blending method (knitting method or mesh pattern) for the metal fibers 52 and the resin fibers 50 in the braid 42 is not particularly limited, and thus desirably determined as appropriate such that the rigidity of the flexible tube 26 and the bonding strength between the braid 42 and the outer skin 44 resulting from the bonding between the resin fibers 50 and the outer skin 44 is sufficiently ensured.

As illustrated in FIG. 5, the braid 42 preferably has a single-layer structure in a viewpoint of reducing the size and weight of the flexible tube 26 and suppressing a manufacturing cost of the flexible tube 26. However, the structure of the braid 42 may be determined based on the rigidity of the flexible tube 26 and the completed size thereof.

After the braid 42 is formed as described above, in STEP 4, the outer circumferential surface of the spiral tube 40 is covered with the braid 42 to form the inner tube 48.

The spiral tube 40 may be a spiral tube which is generally used for the flexible tube for the endoscope 10 as long as the spiral tube can accommodate and protect the lightguide, the air/water supply channel, the forceps channel, and the cable.

If necessary, the spiral tube 40 deposited with a release agent may be used.

In this case, the release agent deposited on the spiral tube 40 may be a known release agent such as a release agent deposited on the metal fibers as described before. A method of depositing the release agent on the spiral tube 40 may be a known method.

An example of the method of covering the outer circumferential surface of the spiral tube 40 with the braid 42, which can be employed, includes a method of inserting the spiral tube 40 into the inside of the braid 42 having the tubular shape and then extending the braid 42 by suitable means until a gap between the spiral tube 40 and the braid 42 disappears, thereby bringing the braid 42 into close contact with the outer circumferential surface of the spiral tube 40.

Next, in STEP 5, the outer circumferential surface of the braid 42 is covered with the outer skin 44.

The outer skin 44 may be made of any resin, as long as the resin can protect an inner portion of the flexible tube 26, and does not harm a living body when the endoscope 10 is inserted into the body.

The resin forming the outer skin 44 is not particularly limited, and a polyurethane resin, synthetic resins such as vinyl chloride, nylon, polyester, and polytetrafluoroethylene, polystyrene-based resins, polyethylene-based resins, polypropylene-based resins, polyester-based resins, polyurethane-based resins, polyamide-based resins, polyvinyl chloride-based resins, fluorine-based resins, mixtures thereof, and the like are suitable examples.

A method of forming the outer skin 44 is not particularly limited. The outer skin 44 having a hollow tube shape may be formed using a known hollow tube manufacturing method, and then the inner tube 48 may be inserted into the outer skin 44. Alternatively, the outer skin 44 may be directly formed on an outer circumferential surface of the inner tube 48 by extrusion molding.

Next, in STEP 6, the braid 42 of the inner tube 48 and the outer skin 44 are bonded to each other.

In this case, it is necessary to bond, to the outer skin 44, only the resin fibers 50 in the braid 42. Therefore, the braid 42 and the outer skin 44 are bonded to each other by heating through the bonding materials 54 deposited on the resin fibers 50.

Specifically, the entire inner tube 48 covered with the outer skin 44 is heated to a temperature of approximately 160° C. to 180° C. to melt the bonding materials 54 and the release agents 56, thereby bonding the resin fibers 50 to the outer skin 44 through the bonding materials 54. Note that the metal fibers 52 are not bonded to the outer skin 44 because of the presence of the release agents 56.

The temperature range of approximately 160° C. to 180° C. is a suitable temperature range within which, in a case where, for example, the bonding materials 54 which are a polyurethane-based resin, the release agents 56 which are a silicon-based resin, and the outer skin 44 which is a polyurethane-based elastomer or a polyester-based elastomer are to be used, when the outer circumferential surface of the inner tube 48 is covered with the outer skin 44, the bonding materials 54 and the release agents 56 are melted so that the resin fibers 50 of the braid 42 are sufficiently bonded to the outer skin 44 by the bonding materials 54 without bonding the braid 42 and the spiral tube 40 to each other, and the release agents 56 serves to prevent the metal fibers 52 of the braid 42 from being bonded to the outer skin 44.

Next, in STEP 7, the outer circumferential surface of the outer skin 44 is covered with the coat layer 46.

The coat layer 46 is a non-cohesive layer and protects the outer skin 44. A material of the coat layer 46 is not particularly limited as long as the material can prevent wastes contained in a body cavity from attaching to an outer surface portion of the endoscope 10, increase a resistance of the endoscope 10 to chemical agents, and improve the sliding of the flexible tube 26 inserted into a body cavity of a patient. A coat layer used for a conventional flexible tube may be used.

A method of forming the coat layer 46 is not particularly limited, and thus the coat layer 46 may be formed using a known method.

A method of covering the outer circumferential surface of the outer skin 44 with the coat layer 46 is not particularly limited, and thus the covering may be performed using a conventional method.

In STEP 8, the outer skin 44 and the coat layer 46 are bonded to each other by a known method to manufacture the flexible tube 26.

When the flexible tube 26 is manufactured using the method as described above, only the resin fibers 50 in the braid 42 can be strongly bonded to the outer skin 44 made of a resin by the bonding materials 54 without bonding the outer skin 44 to the metal fibers 52 having bonding strength (contact strength) which may be reduced because of the lapse of time or moisture. Therefore, it is possible to realize the flexible tube 26 with high endurance in which the rigidity is not reduced because of the use period of the endoscope or the moisture in the use environment thereof.

In the embodiment described above, STEP 1 in which the release agents 56 are deposited on the metal fibers 52 is performed, and then STEP 2 in which the bonding materials 54 are deposited on the resin fibers 50. However, the present invention is not limited thereto. For example, STEP 1 may be performed after STEP 2 is performed. Alternatively, STEP 1 and STEP 2 may be simultaneously performed.

In the embodiment described above, STEP 5 in which the outer circumferential surface of the braid 42 is covered with the outer skin 44 and STEP 6 in which the braid 42 and the outer skin 44 are bonded to each other are separately performed. Alternatively, STEP 5 and STEP 6 may be simultaneously performed.

For example, when the outer skin 44 is directly formed on the outer circumferential surface of the inner tube 48 by extrusion molding, covering and bonding can be simultaneously realized. Specifically, a melted resin may be extruded to the outer circumferential surface of the braid 42 at a uniform thickness by using a known extrusion molding machine to be deposited thereon, and then cooled to thereby directly form the outer skin 44 on the outer circumferential surface of the braid 42.

In this case, the bonding materials 54 previously deposited on the resin fibers 50 and the release agents 56 previously deposited on the metal fibers 52 are melted by heat of the melded resin deposited on the outer circumferential surface of the braid 42, and hence the resin fibers 50 are strongly bonded to the outer skin 44 through the bonding materials 54.

In the embodiment described above, STEP 3 in which the braid 42 is formed is performed, and then STEP 4 in which the outer circumferential surface of the spiral tube 40 is covered with the braid 42 is performed. However, the present invention is not limited thereto. Alternatively, STEP 3 and STEP 4 may be simultaneously performed. For example, the resin fibers 50 deposited with the bonding materials 54 and the metal fibers 52 deposited with the release agents 56 can be blended by using the machine as illustrated in FIG. 7 to directly form the braid 42 on the outer circumferential surface of the spiral tube 40.

In the embodiment described above, STEP 4 in which the outer circumferential surface of the spiral tube 40 is covered with the braid 42 is performed, and then STEP 5 in which the outer circumferential surface of the braid 42 is covered with the outer skin 44 is performed. However, the present invention is not limited thereto. For example, the outer circumferential surface of the braid 42 may be covered with the outer skin 44, and then the outer circumferential surface of the spiral tube 40 may be covered with the braid 42 covered with the outer skin 44.

The flexible tube for an endoscope and the method of manufacturing the flexible tube for an endoscope according to the embodiment are described in detail. The present invention is not limited to the embodiment described above. Various changes and modifications can be made without departing from the spirit of the present invention.

What is claimed is:

1. A flexible tube for an endoscope, comprising:
   a spiral tube including a band-shaped plate which is spirally wound;
   a braid which covers an outer circumferential surface of the spiral tube, the braid having a structure in which metal fibers deposited with a release agent and heat-resistant resin fibers deposited with a bonding material are blended in a mesh pattern; and
   an outer skin made of a resin, which covers an outer circumferential surface of the braid,
   wherein the resin fibers of the braid are bonded to the outer skin by the bonding material while the metal fibers are not bonded to the outer skin due to the release agent.

2. The flexible tube according to claim 1, wherein, of the metal fibers and the resin fibers which are included in the braid, only the resin fibers are bonded to the outer skin through the bonding material.

3. The flexible tube according to claim 1, wherein the braid has a single-layer structure.

4. The flexible tube according to claim 1, wherein the bonding material deposited on the resin fibers have a weight equal to or larger than 10% of a weight of the resin fibers.

5. The flexible tube according to claim 1, further comprising a coat layer which covers an outer circumferential surface of the outer skin.

* * * * *